United States Patent
Hebekeuser et al.

(12) 
(10) Patent No.: US 6,313,334 B1
(45) Date of Patent: Nov. 6, 2001

(54) FERROCENE DICARBOXYLIC ACID DIESTERS AND SOLID COMPOSITE PROPELLANTS CONTAINING THE SAME

(75) Inventors: Hans-Peter Hebekeuser, Siegburg; Hans-Peter Mackowiak, Bergisch-Gladbach; Klaus Gottlieb, Herdecke; Hubert Jungbluth, Kaarst; Horst Neitsch, Gelsenkirchen, all of (DE)

(73) Assignees: Dynamit Nobel GmbH Explosivstoff - und Systemtechnik, Troisdorf; Chemische Betriebe Pluto GmbH, Herne, both of (DE)

( * ) Notice: Subject to any disclaimer, the term of this patent is extended or adjusted under 35 U.S.C. 154(b) by 0 days.

(21) Appl. No.: 09/423,384

(22) PCT Filed: May 2, 1998

(86) PCT No.: PCT/EP98/02600

§ 371 Date: Jun. 7, 2000

§ 102(e) Date: Jun. 7, 2000

(87) PCT Pub. No.: WO98/50396

PCT Pub. Date: Nov. 12, 1998

(30) Foreign Application Priority Data

May 7, 1997 (DE) .............................................. 197 19 126

(51) Int. Cl.[7] .............................. C07F 17/02; C10L 1/30; C06B 45/10

(52) U.S. Cl. .............................. 556/145; 149/19.2; 44/361

(58) Field of Search .......................... 556/145; 149/19.2; 44/361

(56) References Cited

U.S. PATENT DOCUMENTS

| | | | |
|---|---|---|---|
| 3,558,680 | * | 1/1971 | Moffett et al. ........................ 260/439 |
| 3,932,240 | * | 1/1976 | Braun et al. ......................... 149/19.2 |

FOREIGN PATENT DOCUMENTS

2733752-A1 * 11/1996 (FR) .

OTHER PUBLICATIONS

Chemical Abstracts, vol. 127, No. 3, abstract No. 36710m, (Jul. 21, 1997).*

* cited by examiner

*Primary Examiner*—Porfirio Nazario-Gonzalez
(74) *Attorney, Agent, or Firm*—Antonelli, Terry, Stout & Kraus, LLP

(57) ABSTRACT

Ferrocene dicarboxylic acid diesters have the general formula (I), in which X stands for an oligoethylene glycol radical with 2 to 20 ethoxyl units and/or an $\alpha,\omega$-alkyldiol radical with 2 to 18 C atoms. Also disclosed are processes for preparing the same, their use, solid composite propellants containing the disclosed ferrocene dicarboxylic acid diesters and processes for preparing the same.

31 Claims, No Drawings

FERROCENE DICARBOXYLIC ACID DIESTERS AND SOLID COMPOSITE PROPELLANTS CONTAINING THE SAME

The invention relates to ferrocene dicarboxylic acid diesters having the general formula

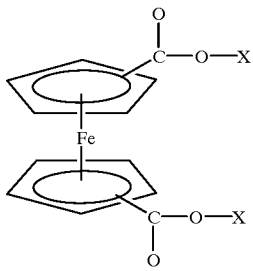

to processes for preparing the same, their use, solid composite propellants containing the ferrocene. dicarboxylic acid diesters in accordance with the invention, and to processes for preparing the same.

Ferrocenyleaters are known in principle from the prior art, for example 2(2-n-butoxyethoxy)ethyl ferrocene from U.S. Pat. No. 3,558,680, which can be prepared from ferrocene carboxylic acid and 2(2-n-butoxyethoxy) ethanol.

Ferrocene derivatives are used in the widest variety of fields, among others also as combustion moderators for solid propellants. Most of the known ferrocene-containing combustion moderators, however, display the unwanted property of migration, i.e. they travel out of the rubber-like binder matrix of the solid propellant into the surrounding insulation material, which leads to an uneven combustion and to a worsening of the resistance to ageing of the solid propellant.

In order to solve this problem, relatively complex ferrocene, derivatives were developed, which have a clearly reduced migration behaviour, or even none at all, such as, for example, so-called butacene (see EP 0 169 130 and BP 0 171 307). Apart from the difficult and complex preparation processes, these derivatives, in comparison with the migrating ferrocene derivatives, display a worse combustion as combustion moderators.

Developments (for example U.S. Pat. No. 3,932,240) for binding ferrocene derivatives having terminal hydroxyl groups or isocyanate groups by reaction to the plastic matrix of the solid propellants also exist. However, these combustion moderators also display an unsatisfactory combustion.

The object of the present invention is to make available ferrocene dicarboxylic acid diesters which, in solid propellants, have no tendency to migrate and nevertheless have a good to excellent combustion behaviour. In particular, they are to be suitable as combustion moderators for solid propellants. Furthermore, they are to have a low viscosity and a low vapour pressure.

This object was achieved in accordance with the invention by ferrocene dicarboxylic acid diesters having the general formula

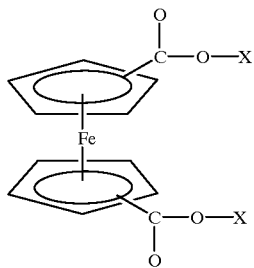

in which X is an oligoethylene glycol radical having 2 to 20 ethoxy units and/or an α,ω-alkyldiol radical having 2 to 8 C atoms.

Of the ferrocene dicarboxylic acid diesters in accordance with the invention, those in which X is an oligoethylene glycol radical having 2 to 4 ethoxy units are particularly preferred, This compound has particularly favourable properties, in particular with respect to the viscosity and the vapour pressure. For the same reasons, of the ferrocene dicarboxylic acid diesters in accordance with the invention that have an α,ω-alkyldiol radical, the compounds in which the alkyldiol radical has 2 to 8 C atoms are particularly suitable. In this connection, the aliphatic chain of the alkyldiol radicals having 3 to 8 C atoms can even be branched. However, compounds having a linear carbon chain are preferred.

A suitable way for preparing the ferrocene dicarboxylic acid diesters in accordance with the invention is the synthesis by way of the ferrocene di(carboxylic acid chloride). As a rule, an excess of the corresponding diol or glycol compound is used in this connection. However, a process which starts from the corresponding ferrocene dicarboxylic acid is preferred. As a rule, a stoichiometric excess of the diol or glycol compound is used here as well.

Usually, as a result of the low carbonyl activity, carboxylic acids generally react only slowly with alcohols. By adding catalysts, usually typical esterification catalysts, in particular anhydrous hydrogen chloride, the esterification can be accelerated considerably. In this connection, the reaction mixture can be saturated with dry hydrogen chloride gas at the start of the reaction, or dry hydrogen chloride gas can even be passed through the reaction mixture throughout the entire reaction.

The ferrorene dicarboxylic acid diesters in accordance with the invention can be used in solid composite propellants, among other things.

A further object therefore consisted in preparing solid composite propellants which do not have the disadvantages of the solid composite propellants known from the prior art but which distinguish themselves by an improved combustion behaviour.

This object was achieved in accordance with the invention by a solid composite propellant having the features of claim 6. Advantageous developments are characterised in claims 7 to 25.

Because the ferrocene dicarboxylic acid diesters in accordance with the invention have a liquid and not too highly viscous consistency and can be mixed with the binder polymers of the solid composite propellants and have, by way of their terminal OH groups, an unambiguously reproducible bonding functionality with constant equivalence values, they ensure a uniform casting viscosity for the fully mixed propellant slurry without negatively influencing the hardening reaction or the pot time. Moreover, they display no substantial impairment of the rubber-like properties of the binder polymers, for example by increasing the cross-linking density. They are oxidation-stable in the solid composite propellant matrix, so the stability of the solid composite propellant is not impaired The safety-related properties of the solid composite propellant are not negatively influenced by the binding in of the substances in accordance with the invention.

The ferrocene dicarboxylic acid diester derivatives in accordance with the invention are used as combustion moderators in the solid composite propellant. In this connection, the binding agent used in the solid composite propellant fixes the ferrocene dicarboxylic acid diester derivatives in accordance with the invention by way of their terminal hydroxyl groups.

Suitable polymer binders for the solid composite propellants in accordance with the invention consist of pre-polymers having terminal hydroxyl groups, which are converted with suitable linking reagents to form the actual binding agent. Examples of such pre-polymers are polyurethane binders such as polybutadiene (HTPB), polyester polyols or polyether polyols. Coupling reagents to be used are, for example, bifunctional or trifunctional isocyanates, preferably isophoron diisocyanate (IPDI), hexamethylene diisocyanate (HDI), toluene diisocyanate (TDI) or mixtures of the same. Particularly preferably, toluene diisocyanate (TDI) is used, In order to improve the network formation, when bifunctional isocyanates are used, low-molecular triols, for example trimethylolpropane, trimethylolethane or 1,2,4-butane triol, trifunctional polyethers orpolyesters can be used in a molar concentration corresponding substantially to the ferrocene dicarboxylic acid diester derivative, As polyurethane pre-polymers, preferably polybutadienes (HTPB) having terminal hydroxyl groups having an average molecular weight of 400 to 4,000, preferably 1,000 to 3,000, come into question.

In addition to these binding agents consisting of pre-polymers having terminal hydroxyl groups and the bifunctional or trifunctional isocyanates, polymer binders consisting of a cross-linkable mixture of hydroxyl-group-containing polymers and a polymer based on a 1,3-butadiene having lateral-position succinic anhydride groups have proven to be particularly suitable. These polymer binders harden in the presence of heat. The use of such polymers as binding agents for propellant bodies is described in DE-PS 38 09 297. The hydroxyl-group-containing polymer generally has an average molecular weight of between 1,000 and 10,000 and a hydroxyl number between 5 and 200 [mg KOH/g]. A hydroxyl-group-containing polybutadiene is particularly preferred. Other hydroxyl-group-containing polymers which are liquid at room temperature can also be used. These include the polyester polyols or polyether polyols already mentioned above, the polyethylene polyols or the polypropylene polyols. The reaction partner based on the 1,3-butadiene having lateral-position succinic anhydride groups is generally also known as maleinised butadiene polymer.

The composite solid propellant in accordance with the invention contains as energy-rich fuels crystalline explosives, for example the nitramines hexogen or octogen, aromatic or aliphatic nitro compounds or amino nitro compounds, the use of which in propellants is known per se. Mixtures of the explosives can also be used. A crystalline inorganic oxidising agent from the group of alkali, alkaline earth and ammonium chlorates, perchlorates or nitrates, preferably ammonium perchlorate (AP) or ammonium nitrate (AN), or mixtures of these oxidising agents can be used as an oxidising agent. A preferred composition of the solid composite propellant consists of 40 to 85% by weight of the energy-rich fuel, 1 to 40% by weight of the oxidizing agent, 10 to 45% by mass binding agent and 0.1 to 10% by weight of the ferrocene dicarboxylic acid diester derivative in accordance with the invention.

Conventional additives, such as antioxidants, stabilisers, plasticisers and/or adhesion promoters, for example, can be added if appropriate. The substances to be used are known to the skilled person. In order to increase the output, added substances which are known per se, for example metal powders such as aluminium, magnesium, titanium, boron and/or iron, can be added if appropriate. The type and amount of the additives/added substances to be used depends on the fuel or oxidising agent chosen. Generally, the amount of additives is between 0.1 and 2.0% by weight and the amount of the added substances can constitute up to 15%, in each case with respect to the solid composite propellant. In addition to the combustion moderators in accordance with the invention, other combustion moderators which are known per se and emulsifiers and lubricants can also be used. Mixtures of the above-mentioned components can also be used.

The solid composite propellants in accordance with the invention having a binder consisting of a pre-polymer having terminal hydroxyl groups and isocyanates as linking reagents can be prepared by mixing the liquid pre-polymer with the ferrocene dicarboxylic acid diester derivative in accordance with the invention, the fuel and the coupling reagent to form a slurry and binding the ferrocene dicarboxylic acid diester derivative into the binder. The addition of the linking reagent can also take place after the other components have been mixed.

The preparation of the composite propellants in accordance with the invention having a polymer binder consisting of a cross-linkable mixture of hydroxyl-group-containing polymers and a polymer based on a 1,3-butadiene having lateral-position succinic anhydride groups takes place in a manner known per se. All the components can be mixed together. Particularly advantageous in the use of this polymer-binding system is the fact that the mixture which is obtained can be stored in the non-cross-linked state for a comparatively long time without negative changes occurring. The mixture is then kneaded thoroughly at room temperature and then pressed to form solid composite propellant moulded articles having the desired dimensions, for example pressed to form strands After this shaping, the polymer binder is hardened by heat treatment. The hardening temperature depends on the binding-agent system that is chosen. It is generally above 35° C. The upper limit of the hardening temperature is to be clearly below the detonation or decomposition temperature of the fuel which is used.

In addition to the use as combustion moderators in solid composite propellants, the ferrocene dicarboxylic acid diesters in accordance with the invention can also be used as non-halogenated reactive flame retardants and as surfactants.

The invention is to be explained in greater detail with the aid of the following examples without thereby restricting it:

EXAMPLE 1

Composition

| | |
|---|---|
| 10.0g | ferrocane di(carboxylic acid chloride) (>97%) |
| 29.0g | 1,4-butane diol in the molar ratio 1:10 |
| 10 | drops pyridine |

The educts are placed in a backflow reaction apparatus, heated to 60° C. whilst stirring and kept at this temperature for 6 hours. The reaction product is then mixed with 500 ml methylene chloride, washed with saturated sodium bicarbonate solution and the organic phase is separated from the aqueous phase. The organic phase is purified, washed in a pH-neutral manner with distilled $H_2O$ and filtered. The solvent is removed and the ferrocene di(carboxylic acid hydroxybutyl eater) which is obtained as residue is weighed out (11.9 g).

The yield amounts to 88.5% with respect to ferrocene di(carboxylic acid chloride).

EXAMPLE 2

Composition

| | | |
|---|---|---|
| a) | 10.0g | ferrocene di(carboxylic acid chloride) (>97) |
| | 29.0g | ethylene glycol in the molar ratio 1:10 |
| | 10 | drop pyridine |
| b) | 20.0g | ferrocene di(carboxylic acid chloride) (>95%) |
| | 68.3g | diethylene glycol in the molar ratio 1:0 |
| | 20 | drops pyridine |
| c) | 20.0g | ferrocene di(carboxylic acid chloride) (>95%) |
| | 124.9g | tetraethylene glycol in the molar ratio 1:10 |
| | 20 | drop pyridine |

Reaction carried out as in Example 1.

Weigh out:

| | | | |
|---|---|---|---|
| a) | ferrocene di(carboxylic acid monoethylene glycol ester): | 11.2 | g |
| | yield of ester wih repect to ferrocene di(carboxyiic acid chloride): | 96.6% | |
| b) | ferrocene di(carboxylic acid diethylene glycol ester): | 27.1 | g |
| | yield of ester with respect to ferrocene di(carboxylic acid chloride): | 93.6 | % |
| C) | ferrocene di(carboxylic acid tetraethylene glycol ester): | 39.1 | g |
| | yield of ester with repect to ferrocene di(carboxylic acid chloride): | 97.0 | % |

EXAMPLE 3

The experimenting apparatus comprised a multi-necked flask with stirrer, thermometer, backflow cooler and gas distribution tube,

Composition 27.4 g ferrocene dicarboxylic acid 212.2 g diethylens glycol

EXPERIMENT 1

The amounts given above were placed in the flask and, whilst stirring for 3 hours, heated to 80° C. During this time, a hydrogen-chloride gas current was continuously passed into the mixture. After cooling, the solution was thinned with 500 ml methylene chloride and filtered. The solution was shaken with aqueous sodium bicarbonate solution and then washed to neutral with water, dried over sodium sulphate and filtered. After the solvent had been decanted, 34.1 g of a fluid, dark brown clear liquid were obtained. The NMR spectroscopic analysis indicated a purity of 80 to 90% by weight, which corresponds to a yield of 68.3% by mole.

EXPERIMENT 2

The amounts indicated above were placed in the flask, the mixture was saturated with dry hydrogen chloride gas and heated for 5 hours to 80° C. The processing took place as in Test 1. A residue of 35.6 g was obtained.

This was clear, dark brown and fluid. The NMR spectroscopic analysis indicated a purity of 80 to 95% by weight, which corresponds to a yield of 75.2% by mole.

Preparation of the Composite Solid Propellants

The components to be used were mixed in the desired mixing proportion, the mixture was kneaded for approximately 30 minutes at root temperature and then pressed into the desired shape, for example to form strands. The solid composite propellants obtained are elastic even at temperatures as law as −40° C. and show no brittle fracture. In order to determine the warm storage performance, samples were tempered at 105° C. for 78 hours, The weight loss was then determined in the so-called Holland test. A significant weight loss could not be observed in any of the solid composite propellants in accordance with the invention. The following table gives some compositions for solid composite propellants in accordance with the invention, as well as the combustion rates determined at 20° C. and the pressure exponents.

| binding agent | hexogen [% by wt.] | AP [% by wt.] | combustion moderator [% by wt.] | | combustion velocity [mm/s] | | | pressure exponent |
|---|---|---|---|---|---|---|---|---|
| | | | | | $r_{60}$ | $r_{90}$ | $r_{120}$ | n |
| A | 50 | 20 | I: | 6 | 14.1 | 15.3 | 17.2 | 0.29 |
| A | 50 | 20 | I: | 10 | 12.1 | 14.5 | 16.4 | 0.44 |
| A | 50 | 20 | II: | 6 | 10.2 | 11.9 | 13.2 | 0.37 |
| A | 50 | 20 | II: | 10 | 11.5 | 11.7 | 13.8 | 0.26 |
| A | 35 | 35 | II: | 6 | 17.3 | 18.7 | 20.4 | 0.26 |
| A | 35 | 35 | I: | 6 | 20.3 | 19.3 | 19.3 | — |
| B | 35 | 35 | I: | 6 | 21.0 | 23.6 | 28.6 | 0.45 |
| C | 50 | 20 | I: | 6 | 10.8 | 12.4 | 13.8 | 0.35 |
| C | 50 | 20 | II: | 6 | 9.6 | 12.2 | 13.5 | 0.49 |
| D | 50 | 20 | I: | 6 | 17.1 | 21.4 | 28.0 | 0.71 |
| D | 50 | 20 | II: | 6 | 9.7 | 12.2 | 13.4 | 0.47 |
| B | 50 | 20 | II: | 6 | 10.0 | 12.5 | 13.7 | 0.46 |
| E | 50 | 20 | II: | 10 | 11.3 | 14.0 | 16.1 | 0.51 |
| E | 50 | 20 | I: | 10 | 14.9 | 17.6 | 19.5 | 0.39 |

Legend:
A = polybutadiene; viscosity: 35 pascal × sec (20° C.)
B = polybutadiene; viscosity: 1.9 pascal × sec (25° C.)
C = polybutadiene; viscosity: 55 poise (25° C.)
D = polybutadiene; viscosity: 200–300 poise (25° C.)
E = polybutadiene; viscosity: 0.4 pascal × sec (25° C.)
I: = combustion moderator: ferrocene dicarboxylic acid bis(diethylene glycol) ester
II: = combustion moderator: ferrocene dicarboxylic acid bis(tetraethylene glycol) ester

What is claimed is:

1. Ferrocene dicarboxylic acid diesters having the general formula

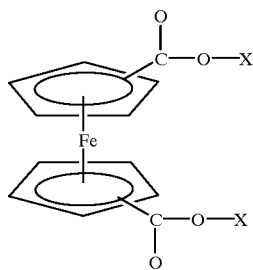

in which X is an oligoethylene glycol radical having 2 to 20 ethoxy units and/or an α,ω-alkyldiol radical having 2 to 18 C atoms.

2. Ferrocene dicarboxylic acid diesters according to claim 1, characterised in that the oligoethylene glycol radical has 2 to 4 ethoxy units.

3. Ferrocene dicarboxylic acid diesters according to claim 1, characterised in that the α,ω-alkyldiol radical has 2 to 8 C atoms.

4. Process for preparing farrocene dicarboxylic acids in accordance with claim 1 by reaction of ferrocene di(carboxylic acid chloride) with an oligoethylene glycol having 2 to 20 ethoxyl units and/or an α,ω-alkyldiol having 2 to 8 C atoms.

5. Process for, preparing ferrocene dicarboxylic acid diesters in accordance with claim 1 by reaction of ferrocene dicarboxylic acid with an oligoethylens glycol having 2 to 20 ethoxyl units and/or an α,ω-alkyldiol having 2 to 8 C atoms in the presence of catalysts; preferably anhydrous hydrogen chloride.

6. Solid composit propellant containing at least one oxidising agent, at least one energy-rich fuel, at least one binding agent and at last one ferrocene derivative, characterised in that the ferrocene derivative is a ferrocene dicarboxylic acid diester having the general formula

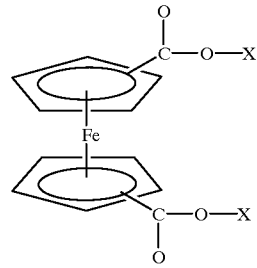

in which X is an oligoethylene glycol radical having 2 to 20 ethoxyl units and/or an α,ω-alkyldiol radical having 2 to 18 C atoms.

7. Solid composite propellant according to claim 6, characterised in that the oligoethylene glycol radical has 2 to 4 ethoxyl units.

8. Solid composite propellant according to claim 6, characterised in that the α,ω-alkyldiol radical has 2 to 8 C atoms.

9. Solid composite propellant according to claim 6, characterised in that a crystalline inorganic oxidising agent from the group of alkali, alkaline earth and ammonium chlorates, perchlorates or nitrates, or mixtures of these oxidising agents is used as an oxidising agent.

10. Solid composite propellant according to claim 6, characterized in that ammonium perchlorate (AP) or ammonium nitrate (AN) is used as an oxidising agent, or in that mixtures of these oxidizing agents are used.

11. Solid composite propellant according to claim 6, characterised in that crystalline explosives from the group of nitramines, aromatic or aliphatic nitro compounds or amino nitro compounds, or mixtures of these fuels, are used as a fuel.

12. Solid composite propellant according to claim 6, characterised in that there is used as a fuel hexogen or octogen, or in that mixtures of these oxidising agents are used.

13. Solid composite propellant according to claim 6, characterised in that polymer binders which can be prepared from pre-polymers having terminal hydroxyl groups and suitable coupling reagents are used as a binding agent.

14. Solid composite propellant according to claim 6, characterised in that polyurethane binders are used as pre-polymers and bifunctional or trifunctional isocyanates, preferably isophorone diisocyanate (IPDI), hexamethylene diisocyanate (HDI), toluene diisocyanate (TDI) or mixtures of the same are used as coupling agents.

15. Solid composite propellant according to claim 6, characterised in that polybutadiene (HTPB), polyester polyols or polyether polyols are used as polyurethane binders, and toluene duisocyanate (TDI) is used as a coupling reagent.

16. Solid composite propellant according to claim 6, characterised in that, when bifunctional isocyanates are used as a coupling reagent, low-molecular triols from the group trimethylolpropane, trimethylolethane, 1,2,4-butane triol are used, or in that trifunctional polyethers or polyesters are used in a molar concentration corresponding substantially to the ferrocene dicarboxylic acid diester.

17. Solid composite propellant according to claim 6, characterized in that the polybutadiene (HTPB) having terminal hydroxyl groups has an average molecular weight of 400 to 4,000, preferably 1,000 to 3,000.

18. Solid composite propellant according to claim 6, characterised in that polymer binders which can be prepared from a cross-linkable mixture of hydroxyl-group-containing polymers and a polymer based on a 1,3-butadiene having lateral-position succinic anhydride groups are used as binding agents.

19. Solid composite propellant according to claim 18, characterized in that the hydroxyl-group-containing polymer is selected from polybutadienes, polyester polyols, polyether polyols, polyethylene polyols or polypropylene polyols.

20. Solid composite propellant according to claim 18, characterised in that the hydroxyl-group-containing polymer has an average molecular weight of between 1,000 and 10,000 and a hydroxyl number between 5 and 200.

21. Solid composite propellant according to claim 6, characterized in that additives and/or output-increasing components are additionally used.

22. Solid composite propellant according to claim 6, characterised in that antioxidants, otabilisers, plasticisers and adhesion promoters, and/or as output-increasing components metal powders, preferably aluminium powder, magnesium powder, titanium powder, boron powder and iron powder are used as additives.

23. Solid composite propellant according to claim 6, characterised in that it consists of 40 to 85% by wt. of the energy-rich fuel, 1 to 40% by wt. of the oxidising agent, 10 to 45% by wt. of binding agent and 0.1 to 10% by wt. of the ferrocene dicarboxylic acid diester in accordance with one of claim 1 to 3.

24. Solid composite propellant according to claim 6, characterized in that it additionally contains antioxidants, stabilisers, plasticisers and adhesion promoters in amounts of 0.1 to 2.0% by wt., with respect to the solid composite propellant.

25. Solid composite propellant according to claim 6, characterized in that it additionally contains, as output-increasing components metal powder, preferably aluminium powder, magnesium powder, titanium powder, boron powder and iron powder in amounts of up to 15% by wt., with respect to the solid composite propellant.

26. Process for preparing a solid composite propellant according to claim 6 characterized in that the liquid pre-polymer is mixed with the ferrocene dicarboxylic acid diester, the oxidising agent, the fuel and the additives and/or output-increasing added substances to be used if appropriate, to form a slurry and the ferrocene dicarboxylic acid diester is bound into the binder preferably after addition of the hardener.

27. Process for preparing a solid composite propellant according to claim 18, characterised in that the binding agent consisting of a cross-linkable mixture of hydroxyl-group-containing polymers and a polymer based on a 1,3-butadiene having lateral-position succinic anhydride groups is mixed with the ferrocene dicarboxylic acid diester according to one of claims 1 to 3, the oxidising agent, the fuel and the additives and/or output-increasing added substances to be used if appropriate, the mixture is kneaded at room temperature, pressed to form solid composite propellant moulded articles having the desired dimensions, and the polymer binder is then hardened by heat treatment.

28. A method of providing a non-halogenated flame retardant in a material, the method comprising the step of incorporating a ferrocene dicarboxylic acid diester of claim 1 in the material.

29. A method of providing a surfactant in a material, the method comprising the step of incorporating a ferrocene dicarboxylic acid diester of claim 1 in the material.

30. A method of providing a combustion modifier in a solid composite propellant, the method comprising the step of incorporating a ferrocene dicarboxylic acid diester of claim 1 in the solid composite propellant.

31. The method of claim 30 wherein the ferrocene dicarboxylic acid diester is incorporated in the solid composite propellant in the amount of 0.1 to 10% by wt.

* * * * *